(12) United States Patent
Schlingensiepen et al.

(10) Patent No.: US 7,910,563 B2
(45) Date of Patent: Mar. 22, 2011

(54) ANTISENSE OLIGONUCLEOTIDE TO INHIBIT MELANOMA INHIBITORY ACTIVITY, MIA

(75) Inventors: Karl-Hermann Schlingensiepen, Donaustauf (DE); Reimar Schlingensiepen, Regensburg (DE)

(73) Assignee: Antisense Pharma GmbH, Regensburg (DE)

( * ) Notice: Subject to any disclaimer, the term of this patent is extended or adjusted under 35 U.S.C. 154(b) by 0 days.

(21) Appl. No.: 10/567,879

(22) PCT Filed: Aug. 11, 2004

(86) PCT No.: PCT/EP2004/006986
§ 371 (c)(1),
(2), (4) Date: Apr. 16, 2007

(87) PCT Pub. No.: WO2005/014812
PCT Pub. Date: Feb. 17, 2005

(65) Prior Publication Data
US 2007/0299022 A1     Dec. 27, 2007

(30) Foreign Application Priority Data
Aug. 12, 2003  (EP) .................................... 03018285

(51) Int. Cl.
C07H 21/00   (2006.01)
C07H 21/02   (2006.01)
C12N 15/11   (2006.01)
A61K 48/00   (2006.01)

(52) U.S. Cl. ..... 514/44; 536/23.1; 536/24.3; 536/24.33; 536/24.5

(58) Field of Classification Search ................ 536/23.1, 536/24.3, 24.33, 24.5; 514/44
See application file for complete search history.

(56) References Cited

FOREIGN PATENT DOCUMENTS

| | | |
|---|---|---|
| WO | WO 99/50411 | 10/1999 |
| WO | WO 99/65928 | 12/1999 |
| WO | WO 01/68122 | 9/2001 |
| WO | WO 01/77384 A2 * | 10/2001 |
| WO | WO 2005/014812 | 2/2005 |

OTHER PUBLICATIONS

Jachimczak et al. Inhibition of Immunosuppressive Effects of Melanoma-Inhibiting Activity (MIA) by Antisense Techniques. Int. J. Cancer, 2005 vol. 113:88-92.*
EPO, European Search Report, EP Application No. 03018285.1-2107, dated Feb. 12, 2004.
Golob et al, Characterization of a Transcription Factor Binding Site, Specifically Activating MIA Transcription in Melanoma, J Invest Ermatol 115:42-47, 2000.
PCT, International Search Report, PCT Application No. PCT/EP2004/008986, mailed on Mar. 29, 2005.
Bogdahn, U. et al. / Autocrine Tumor Cell Growth-Inhibiting Activities . . . / Cancer Research, 1989. 49 (19): 5358-5363.
Weilbach, F.X. et al. / Melanoma-Inhibiting Activity Inhibits Cell . . . . Cancer Research, 1990. 50 (21): 6981-6986.
Blesch, A. et al. / Cloning of a Novel Malignant Melanoma-Derived Growth-Regulatory Protein, MIA. / Cancer Research, 1994. 54(21): 5695-5701.

(Continued)

*Primary Examiner* — Sean McGarry
*Assistant Examiner* — Terra Cotta Gibbs
(74) *Attorney, Agent, or Firm* — Thompson Hine LLP

(57) ABSTRACT

An antisense oligonucleotide selected from the group of
  the sequence 5'-TTG CAT AAA CCC AAG GAG-3' (SEQ ID NO: 1) and modifications thereof
  a fragment having at least 8 nucleotides of the sequence 5'-TTG CAT AAA CCC AAG GAG-3' (SEQ ID NO: 1) and modifications thereof.

17 Claims, 2 Drawing Sheets

OTHER PUBLICATIONS van Groningen, JJ, et al. / Identification of Melanoma Inhibitory Activity and Other Differentially Expressed . . . / Cancer Research, 1995. 55(24): 6237-6243.

Bosserhoff, AK et al. / [MIA ("melanoma inhibitory activity"). Biological functions and clinical relevance in malignant melanoma]. Hautarzt, 1998. 49(10): 762-769.

Guba, M. et al. / Overexpression of Melanoma Inhibitory Activity (MIA) Enhances . . . / Br J Cancer, 2000. 83(9): 1216-1222.

Bosserhoff, AK et al. / Functional Role of Melanoma Inhibitory Activity in Regulating Invasion and Metastasis of Malignant Melanoma Cells in Vivo. / Melanoma Res, 2001. 11(4): 417-421.

Stahlecker, J. et al. / MIA as a Reliable Tumor Marker in the Serum of Patients with Malignant Melanoma / Anticancer Res, 2000 20(6D): 5041-5044.

Uhlmann, E. et al. / Antisense Oligonucleotides: A New Therapeutic Principle., Chemical Reviews, 1990. 90(4): 543-584.

Goodchild, J. / Conjugates of oligonucleotides and modified oligonucleotides: a review of their synthesis and properties. Bioconjug Chem, 1990. 1(3): 165-187.

Wagner, V. et al. / Seropositivity for MIA and S100 in Patients with Gastrointestinal Carcinomas. / Med Oncol, 2000. 17(1): 35-38.

Natsume, N. et al. Analysis of Cartilage-Derived Retinoic Acid-Sensitive Protein . . . / Spine, 2001. 26(2): 157-160.

Bosserhoff, AK et al. / Mouse CD-RAP/MIA Gene: Structure, Chromosomal Localization, and Expression . . . / Dev Dyn, 1997. 208(4): 516-525.

Muller-Ladner, U et al. / MIA (melanoma inhibitory activity): a potential serum marker for rheumatoid arthritis, / Rheumatology (Oxford), 1999. 38(2): 148-154.

Bosserhoff, AK et al. / In Situ Expression Patterns of Melanoma-Inhibiting Activity . . . J Pathology, 1999. 187(4): 446-454.

Zhao, Q et al. / Site of Chemical Modifications in CpG Containing Phosphorothioate . . . Bioorg Medical Chem Lett, 1999. 9(24): 3453-3458.

Scaringe, SA / RNA Oligonucleotide Synthesis via 5'-silyl-2-orthoester chemistry / Methods, 2001. 23(3): 206-217.

Flaherty, KT et al. / Antisense Therapeutics: Lessons from early clinical Trials . . . Curr Opin Oncol, 2001. 13(6): 499-505.

* cited by examiner b)

Adenin

Guanin

Cytosin

Thymin c)

Adenin

Guanin

Cytosin

Uracil

ANTISENSE OLIGONUCLEOTIDE TO INHIBIT MELANOMA INHIBITORY ACTIVITY, MIA

FIELD OF THE INVENTION

The present invention relates to an antisense oligonucleotide or modifications thereof for the inhibition of the expression and/or functional activity of Melanoma Inhibitory Activity "MIA", a pharmaceutical composition comprising the oligonucleotide or modifications thereof and its use for the prevention or the treatment of neoplasms, infections and/or immunosuppressive disorders.

BACKGROUND

The polypeptide "Melanoma Inhibitory Activity" MIA, was discovered in 1989 and initially described as a factor that inhibits growth of melanoma tumor cells. The melanoma inhibitory activity (MIA) protein was identified within growth-inhibiting activities purified from tissue culture supernatant of the human melanoma cell line HTZ-19 (Bogdahn et al., Cancer Res. 49: 5358-5363, 1989). Weilbach et al. further demonstrated that MIA inhibits cell proliferation by prolonging of the S-Phase and arrest of the cells in the G2 compartment (Cancer Res. 50; 6981-86. 1990). The antiproliferative action of MIA was also demonstrated in other tumor cells and Peripheral Blood Mononuclear Cells (PBMCs), where recombinant human rMIA inhibited IL-2- or PHA-induced PBMCs proliferation in a dose-dependant manner. Additionally, auto- and allogenic LAK-cytotoxicity was also inhibited by MIA (Jachimczak et al., Proceeding of AACR, 41: 115, 2000).

Blesch et al. identified MIA as a 131-amino acid precursor, processed into a mature 107-amino acid protein. This publication confirmed that MIA acts as a potent tumor cell growth inhibitor for malignant melanoma cell and further extended this observation to other neuroectodermal tumors. They concluded that, " . . . MIA . . . might be attractive as a future antitumor therapeutical substance" (Cancer Res. 54; 5695-5701, 1994).

However, further studies revealed expression patterns inconsistent with a tumor suppressor. In contrast, van Groningen et al. found MIA mRNA expression in non metastasizing cell lines and an inverse correlation of MIA mRNA expression with pigmentation in melanoma metastasis lesions, but notably expression was found to be absent in highly metastasizing cell lines (Cancer Res. 55; 6237-6243, 1995).

More recently, Bosserhoff et al. observed that MIA specifically inhibits attachment of melanoma cells to fibronectin and laminin thereby masking the binding sites of integrins to these extracellular matrix components and promoting invasion and metastasis in vivo (Bosserhoff et al., Hautarzt 49, 762-769, 1998; Stoll et al., EMBO J 20, 340-349, 2001). The growth-inhibitory activity in vitro may therefore reflect the ability of MIA to interfere with the attachment of cells to culture dishes observed by Blesch et al. (Cancer Res. 54; 5695-5701, 1994).

Further experiments performed in hamster by Guba et al. (Brit. J. Cancer 83, 1216-1222, 2000) analyzed the in vivo role of MIA during melanoma metastasis. Enforced expression of MIA in MIA-transfected A-mel3 hamster melanoma cells significantly increased their metastatic potential compared to control transfected cells. In addition, MIA overexpressing cells showed a higher rate of both tumor cell invasion and extravasation. Bosserhoff et al. confirmed these results by the use of stably MIA-transfected BI6 mouse melanoma cells (Bosserhoff et al., Melanoma Res. 11; 417-421, 2001). The capacity of these cells to form lung metastases in syngeneic C57B16 mice was strictly correlated to the level of MIA secretion in mice.

The clinical correlation of MIA expression with melanoma progression was discovered by Bosserhoff et al. (Cancer Res. 57; 3149-53; 1997) and confirmed by others (Stahlecker et al., Anticancer Res. 19; 2691-3, 2000). 81% of the sera obtained from patients with metastasized malignant melanomas in stage III revealed enhanced MIA values and even 97% of the sera from patients in stage IV. Patients in stage I or II disease had only slightly enhanced MIA levels of 13 and 23%, respectively (Bosserhoff et al., Cancer Res. 57; 3149-53; 1997)

Additionally, there is evidence that MIA might be useful as a marker in other types of malignant tumors, since seropositivety was also reported for some patients with advanced gastrointestinal carcinoma with a very poor prognosis (Wagner et al., Med. Oncol. 1735-38, 2000). Recently, MIA levels were measured in cerebrospinal fluid specimens from patients with spinal diseases (Natsume et al., Spine 26(2): 157-60, 2001).

The concentration of MIA in cervical myelopathy, lumbar canal stenosis, and lumbar disc herniation was significantly higher than in the control group. Interestingly, MIA is not expressed in the central nervous system under physiological conditions.

Furthermore, in situ-hybridization experiments, as well as immuno histochemistry localize MIA in the developmental embryo within the growth zone of the skeletal system, and it is being expressed, secreted, and deposited around the chondrocytes. Additionally, it is pathologically expressed in chondrosarcoma (Bosserhoff et al., Dev Dyn 208(4): 516-525, 1997).

Since high levels of MIA were found in chondrocytes, MIA was also investigated as a potential marker for rheumatoid arthritis and cartilage damage. Muller-Ladner et al. found increased MIA serum concentrations in patients with rheumatic diseases with joint destruction, osteoarthritis, HLA-27-associated oligoarthritis, psoriatic arthritis and rheumatic arthritis, where the most significant increase in MIA was found (Muller-Ladner et al., Rheumatology 38; 148-154, 1999).

However, in the case of the tumors, MIA was found to be expressed and secreted into the serum by all of the malignant melanomas examined, but not in other skin tumor, including basal cell cancer and squamous cell cancer, nor in normal melanocytes and keratinocytes (Bosserhoff et al., J Pathol 187(4): 446-454, 1999). Additionally, MIA expression was further found in all advanced stage breast cancer and metastases analyzed suggesting a much broader expression of MIA in malignant epithelial neoplasms than previously determined by serum studies (Bosserhoff et al., J Pathol 187(4): 446-454, 1999).

PRIOR ART

Molecules for the inhibition of the expression and/or functional activity of MIA are published in WO 01/68122. The inhibition is achieved by using at least one nucleic acid molecule, peptide, protein or low molecular weight substance, wherein the nucleic acid molecule is an oligo- or polynucleotide molecule, in particular an antisense molecule and/or ribozyme. The above mentioned patent-application relates to molecules including oligonucleotides able to inhibit the expression and/or function of MIA and thereby reversing the immunosuppression (WO 01/68122).

It was the object of the present invention to develop MIA antisense oligonucleotides with higher efficacy.

BRIEF DESCRIPTIONS OF THE DRAWINGS

FIG. 1 compares the inhibition of MIA expression of the antisense oligonucleotide of the present invention with sequences of prior art.

SUMMARY OF THE INVENTION

Figure 1:
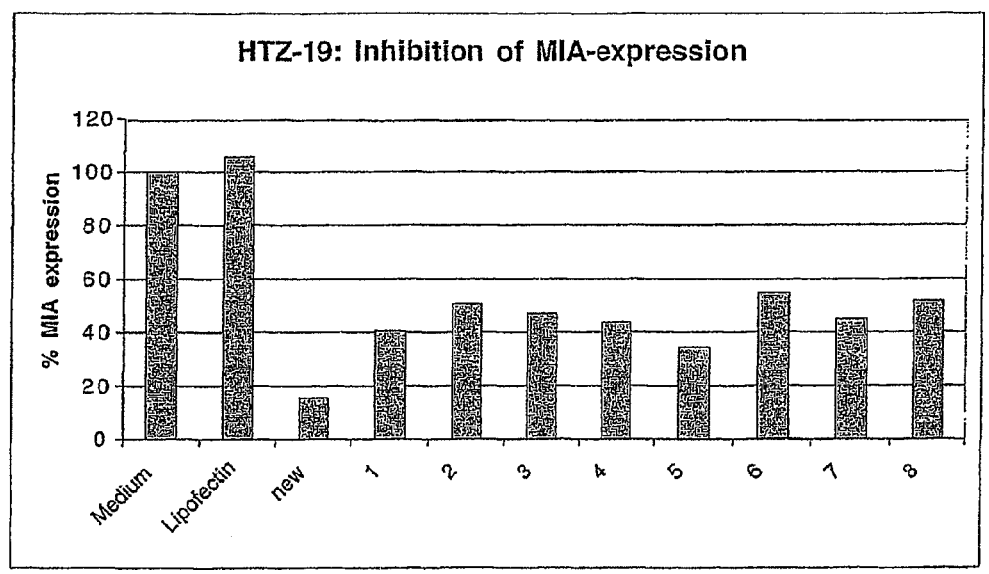

The present invention relates to antisense-oligonucleotides with the following sequence 5'-TTG CAT AAA CCC AAG GAG-3' (SEQ ID NO: 1), modifications thereof, parts of the antisense oligonucleotide with at least 8 nucleotides and/or modifications thereof. They show a surprisingly much more effective inhibition of the expression and/or function of "Melanoma Inhibitory Activity" MIA, thereby eliciting a more effective inhibition of tumor invasion and/or inhibition of metastasis and for a more effective stimulation of immune cells and/or the immune system than antisense-oligonucleotides of the prior art. The present invention also pertains to a pharmaceutical composition comprising at least one of the antisense oligonucleotides or modifications thereof and to its use for the prevention or the treatment of neoplasms, infections and/or immunosuppressive disorders.

Although a number of oligonucleotides have already been tested so far (see WO 01/68122), the antisense oligonucleotide with the sequence 5'-TTG CAT AAA CCC AAG GAG-3' (SEQ ID NO: 1) surprisingly showed the strongest inhibition of MIA compared to the antisense oligonucleotides of the patent application WO 01/68122 with the Sequence-ID-No's 1-8.

DETAILED DESCRIPTION

In one embodiment of the invention, the antisense oligonucleotide having the sequence 5'-TTG CAT AAA CCC AAG GAG (SEQ ID NO: 1) or modifications thereof has a DNA- or RNA-type structure able to hybridize to an area of the gene region coding MIA and thereby reducing and/or inhibiting the expression of MIA. It is also understood by persons skilled in the art that fragments having subsequences of the above given antisense oligonucleotide with at least 8 nucleotides or modifications thereof work according to the invention so long as production of MIA is reduced or inhibited.

In the following, the antisense oligonucleotide with the sequence 5'-TTG CAT AAA CCC AAG GAG (SEQ ID NO: 1) and antisense oligonucleotides representing parts of the sequence with at least 8 nucleotides are referred to as the antisense oligonucleotides.

In another embodiment the antisense oligonucleotides are modified at one or more of the sugar moieties, the bases and/or the internucleotide linkages as well as the phosphate moieties. For example, the modifications of the oligonucleotides comprise modifications such as phosphorothioate (S-ODN) internucleotide linkages, methylphosphonate internucleotide linkages, phosphoramidate linkages, peptide linkages, 2'-O-alkyl modifications of the sugar, in particular methyl, ethyl, propyl, butyl and the like, 2'-methoxyethoxy modifications of the sugar and/or modifications of the bases. The various modifications may be combined in one oligonucleotide.

In one embodiment the ring structure of the ribose group of the nucleotides in the modified oligonucleotide or polynucleotide has the oxygen in the ring structure substituted with N—H, N—R, S and/or methylene.

In other embodiments the backbone modifications include 2'-O-methylribonucleosides (2'-0-Me). These types of substitutions are described extensively in the literature and in particular with respect to their immunostimulating properties in Zhao et al., Bioorganic and Medicinal Chemistry Letters, 1999, 9:24:3453. Zhao et al. describes methods of preparing 2-0-Me modifications to nucleic acids, herein incorporated by reference.

In yet other embodiments, in order to enhance the exonuclease resistance of 2'-substituted oligonucleotides and polynucleotides, the 3' and/or 5' ends of the oligoribonucleotide sequence are preferably attached to exonuclease blocking groups.

A partial list of blocking groups includes inverted bases, 2'- or 3'-O-aryl nucleotides (preferably the aryl is methyl, ethyl or propyl), dideoxynucleotides, methylphosphates, alkyl groups, aryl groups, cordycepin, cytosine arabanoside, phosphoramidates, a peptide linkage, dinitrophenyl group, fluorescein, cholesterol, biotin, biotin analogs, avidin, avidin analogs, strepavidin, acridine, rhodamine, psoralen, glyceryl, methyl phosphonates, butanol, butyl, hexanol, and 3'-O-alkyls.

In a preferred embodiment, at least one blocking group is a biotin, biotin analog, avidin, or avidin analog. These molecules have the ability to both 1) block the degradation of the protected oligonucleotide or polynucleotide and 2) provide means for high affinity attachment of the modified nucleic acids to the solid support. Avidin and biotin derivatives which can be used to prepare the reagents of this invention include streptavidin, succinylated avidin, monomeric avidin, biocytin (biotin-.epsilon.-N-lysine), biocytin hydrazide, amine or sulfhydryl derivatives of 2-iminobiotin and biotinyl-.epsilon.-aminocaproic acid hydrazide. Additional biotin derivatives, such as biotin-N-hydroxysuccinimide ester, biotinyl-.epsilon.-aminocaproic acid-N-hydroxysuccinimide ester, sulfosuccinimidyl 6-(biotin amido)hexanoate, N-hydroxysuccinimideiminobiotin, biotinbromoacetylhydrazide, p-diazobenzoyl biocytin and 3-(N-maleimidopropionyl)biocytin, can also be used as end-blocking groups on the polynucleotides of the present invention.

In a preferred embodiment, at least one end-block on the oligonucleotide is a biotin, biotin analog, avidin, or avidin analog. These molecules have the ability to both 1) block the degradation of the protected oligonucleotide or polynucleotide and 2) provide means for high affinity attachment of the modified nucleic acids to the solid support. Avidin and biotin derivatives which can be used to prepare the reagents of this invention include streptavidin, succinylated avidin, monomeric avidin, biocytin (biotin-.epsilon.-N-lysine), biocytin hydrazide, amine or sulfhydryl derivatives of 2-iminobiotin and biotinyl-.epsilon.-aminocaproic acid hydrazide. Additional biotin derivatives, such as biotin-N-hydroxysuccinimide ester, biotinyl-.epsilon.-aminocaproic acid-N-hydroxysuccinimide ester, sulfosuccinimidyl 6-(biotin amido) hexanoate, N-hydroxysuccinimideiminobiotin, biotinbromoacetylhydrazide, p-diazobenzoyl biocytin and 3-(N-maleimidopropionyl)biocytin, can also be used as end-blocking groups on the polynucleotides of the present invention.

In a preferred embodiment the antisense-oligonucleotides or an effective modification thereof is a phosphorothioate-oligodeoxynucleotide.

Methods for synthesizing antisense-oligonucleotides of the invention are known to those skilled in the art. The principle of one possible synthesis method employs solid phase synthesis using phosphite triester chemistry by growing the nucleotide chain in 3'->5' direction and is described in the following:

The respective nucleotide is coupled to the first nucleoside, which is covalently attached to the solid phase comprising the steps of a) cleaving 5'DMT protecting group of the previous nucleotide
b) adding the respective nucleotide for chain propagation
c) modifying the phosphite group and subsequently cap unreacted 5'-hydroxyl groups
d) repetitive cycles of a) to-c) for the full length oligonucleotide
e) cleaving the oligonucleotide from the solid support
f) followed by working up the synthesis product.

Aryl- and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents.

Methods for making other DNA backbone modifications and substitutions have been described (Uhlmann, E. and Peyman, A., Chem. Rev. 90:544, 1990; Goodchild, J., Bioconjugate Chem. 1:165, 1990).

Additional methods of rendering oligonucleotide or polynucleotide polymers nuclease resistant include, but are not limited to, covalently modifying the purine or pyrimidine bases. For example, bases may be methylated, hydroxy-methylated, or otherwise substituted (e.g., glycosylated) such that the oilgonucleotides or polynucleotides are rendered substantially acid and nuclease resistant.

Other representative heterocyclic bases are disclosed in U.S. Pat. No. 3,687,808, issued to Merigan, et al. The terms "purines" or "pyrimidines" or "bases" are used herein to refer to both naturally-occurring or synthetic purines, pyrimidines or bases.

Figure 2:
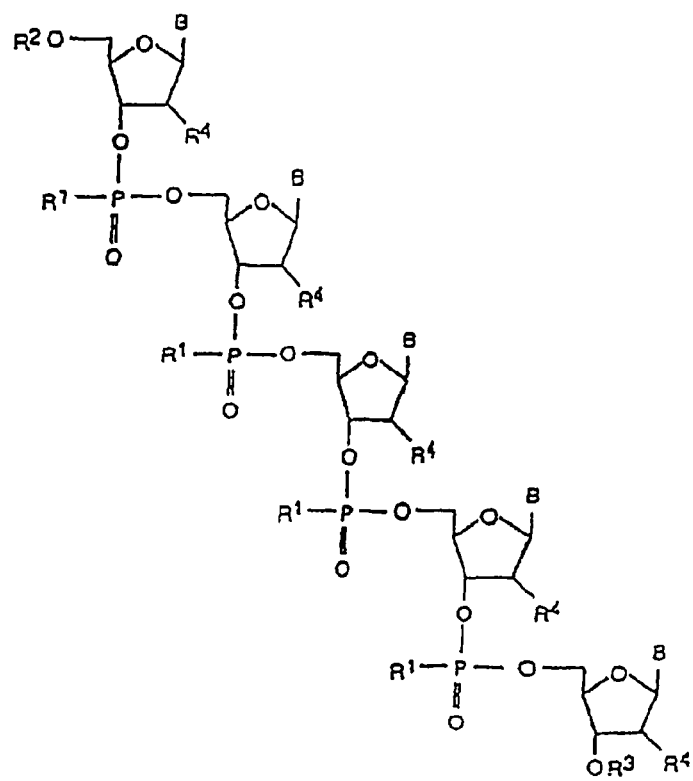
FIG. 2A shows the structure of oligonucleotides.
FIG. 2B shows the structure of oligodeoxyribonucleotide bases.
FIG. 2C shows the structure of oligoribonucleotide bases.
Figure 2:
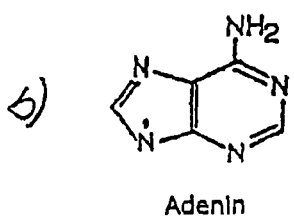
Figure 2:
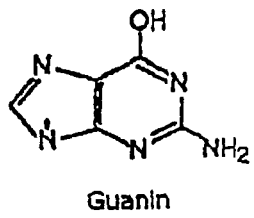
Figure 2:
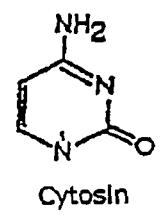
Figure 2:
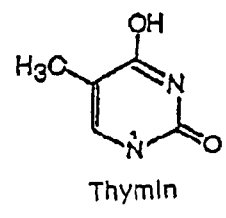
Figure 2:
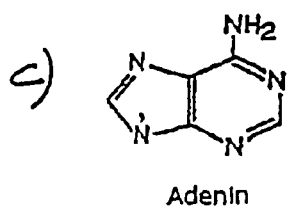
Figure 2:
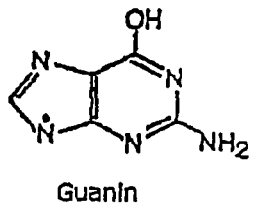
Figure 2:
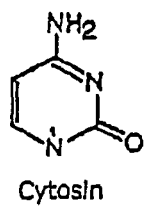
Figure 2:
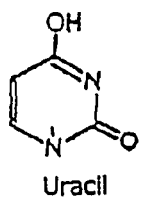

The chemical structure of oligonucleotides and their modifications are given in FIG. 2. The oligonucleotide chain is to be understood as a detail out of a longer nucleotide chain.

In FIG. 2a lit. B means an organic base such as adenine (A), guanine (G), cytosine (C) or thymine (T) (shown in FIG. 2b) in oligodeoxy-ribonucleotides and the bases adenine (A), guanine (G), cytosine (C), uracile (U) (shown in FIG. 2c) in oligo-ribonucleotides. The bases are coupled via the nitrogen N9 in the case of the bases A and G or the nitrogen N1 in the case of the bases C, T and U to the desoxyribose or ribose, respectively. The sequence of the bases is the reverse complement of the genetic target sequence MIA.

The modifications of oligodeoxy-ribonucleotides and oligo-ribonucleotides in FIG. 2a are as follows, whereby both, oligodeoxy-ribonucleotides and oligo-ribonucleotides are referred to as oligonucleotides:

1. Oligonucleotides wherein all $R^1$ are
    1.1 $R^1=O^-M^+$, where all $M^+$ is $Na^+$ or $H^+$
    1.2 $R^1=S^-M^+$, where all $M^+$ is $Na^+$ or $H^+$
    1.3 $R^1=CH_3$
    1.4 $R^1=C_2H_5$
    1.5 $R^1=OCH_3$ or
    1.6 $R^1=OC_2H_5$
2. Oligonucleotides wherein $R^1$ is varied at the internucleotide phosphates within one oligonucleotide. In the following formula, $R^1$ of FIG. 2a) is referred to as $R^{1a}$ or $R^{1b}$.

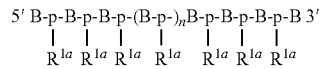

wherein
B=one of the bases A, C, G or T in oligodeoxy-ribonucleotides or accordingly the bases A, C, G or U in oligo-ribonucleotides
p=internucleotide phosphate
$(B-p-)_n$=an oligodeoxy-ribonucleotide or oligo-ribonucleotide stretch wherein
n=1-12, preferably 2-11
$R^{1a}$, $R^{1b}$ are selected from the group of
2.1 $R^{1a}=S^-M^+$, where all $M^+$ is $Na^+$ or $H^+$
$R^{1b}=O^-M^+$, where all $M^+$ is $Na^+$ or $H^+$
2.2 $R^{1a}=CH_3$
$R^{1b}=O^-M^+$, where all $M^+$ is $Na^+$ or $H^+$
2.3 $R^{1a}=S^-M^+$, where all $M^+$ is $Na^+$ or $H^+$
$R^{1b}=CH_3$
2.4 $R^{1a}=CH_3$
$R^{1b}=S^-M^+$, where all $M^+$ is $Na^+$ or $H^+$ 3. Oligodeoxy-ribonucleotides wherein $R^1$ is alternated at the internucleotide phosphates within one oligonucleotide. In the following formula, $R^1$ of FIG. 2a) is referred to as $R^{1a}$ or $R^{1b}$.

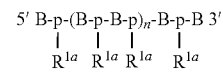

wherein
B=one of the bases A, C, G or T comprised in oligodeoxy-ribonucleotides or accordingly the bases A, C, G or U comprised in oligo-ribonucleotides depending on gene sequence
p=internucleotide phosphate
$(B-p-B-p)_n$=an oligodeoxy-ribonucleotide or oligo-ribonucleotide stretch wherein n=2-8, preferably 3-7
$R^{1a}$, $R^{1b}$ are selected from the group of
3.1 $R^{1a}=S^-M^+$, where all $M^+$ is $Na^+$ or $H^+$
$R^{1b}=O^-M^+$, where all $M^+$ is $Na^+$ or $H^+$
3.2 $R^{1a}=CH_3$
$R^{1b}=O^-M^+$, where all $M^+$ is $Na^+$ or $H^+$
3.3 $R^{1a}=S^-M^+$, where all $M^+$ is $Na^+$ or $H^+$
$R^{1b}=CH_3$ 4. Oligonucleotides or modifications thereof, where $R^2$ is H or covalently coupled cholesterol, poly-(L)lysine or transferrin.

5. Oligonucleotides or modifications thereof, where $R^3$ is H or covalently coupled cholesterol, poly-(L) lysine or transferrin.

6. Any of the modifications described in 1.1-1.6; 2.1-2.4; 3.1-3.3; 4, 5 where all $R^4$ are selected from the group consisting of:
    6.1 $R^4=H$
    6.2 $R^4=F$
    6.3 $R^4=CH_3$
    6.4 $R^4=C_2H_5$
    6.5 $R^4=OH$
    6.6 $R^4=OCH_3$
    6.7 $R^4=OC_2H_5$ Modifications of the antisense-oligonucleotides are advantageous since they are not as fast destroyed by endogeneous factors when applied, as this is valid for naturally occurring nucleotide sequences. However, it is understood by the skilled person that also naturally occurring oligonucleotides having one of the disclosed sequences can be used according to the invention. In a very preferred embodiment the modification is a phosphorothioate modification.

Among several synthesis methods for oligodeoxy-nucleotides known to those skilled in the art, one possible method is described as an example in a greater detail as follows.

Oligodeoxy-nucleotides are synthesized stepwise by 5' addition of protected nucleotides using phosphite triester chemistry. The nucleotide A is introduced as 5'-dimethoxytrityl-deoxyadenosine ($N^4$-benzoyl)-N,N'-diisopropyl-2-cyanoethyl phosphoramidite; the nucleotide C is introduced by a 5'-dimethoxytrityl-deoxycytidine($N^4$-benzoyl)-N,N'-diisopropyl-2-cyanoethyl phosphoramidite; the nucleotide G is introduced as 5'-dimethoxytrityl-deoxyguanosine($N^8$-isobutyryl)-N,N'-diisopropyl-2-cyanoethyl phosphoramidite and the nucleotide T is introduced as 5'-dimethodytrityl-deoxythymidine-N,N'-diisopropyl-2-cyanoethyl phosphoramidite. The nucleotides are preferably applied in 0.1 M concentration dissolved in acetonitrile.

Synthesis can be performed for example on controlled pore glass particles of approximately 150 mm diameter (pore diameter 500 Å) to which the 3' nucleoside is covalently attached via a long-chain alkylamin linker (average loading 30 μmol/g solid synthesis support).

The solid synthesis support is loaded into a cylindrical synthesis column, capped on both ends with filters permitting adequate flow of reagents but hold back the solid synthesis support. Reagents are delivered and removed from the synthesis column using positive pressure of inert gas. The nucleotides are added to the growing oligonucleotide chain in 3'->5' direction. Each nucleotide is coupled using one round of the following synthesis cycle:

Cleavage of the 5'DMT (dimethoxytrityl) protecting group of the previous nucleotide is performed with 3-chloroacetic acid in dichloromethane followed by washing the column with anhydrous acetonitrile. Then one of the bases is added in form of their protected derivative depending on the sequence plus tetrazole in acetonitrile. After reaction the reaction mixture is withdrawn and the phosphite is oxidized with a mixture of sulfur ($S_8$) in carbon disulfid/pyridine/triethylamine. After the oxidation reaction the mixture is withdrawn and the column is washed with acetonitrile. The unreacted 5'-hydroxyl groups are capped with simultaneous addition of 1-methylimidazole and acetic anhydryide/lutidine/tetrahydrofuran. Thereafter, the synthesis column is washed with acetonitrile and the next cycle is started.

The work up procedure and purification of the synthesis products can be carried out as follows:

After the addition of the last nucleotide the deoxynucleotides are cleaved from the solid support by incubation in ammonium solution. Exoxyclic base protecting groups are removed by further incubation in ammonia. Then the ammonium is evaporated under vacuum. Full-length synthesis products still bearing the 5'DMT protecting group are separated from shorter failure contaminants using reverse phase high performance liquid chromatography (HPLC) on reversed phase $C_{18}$ stationary phase. Eluents from the product peak are collected, dried under vacuum and the 5'-DMT protecting group cleaved by incubation in acetic acid, which is evaporated thereafter under vacuum. The synthesis products are solved in deionized water and extracted three times with diethylether. Then the products are dried in vacuum. Another HPLC-AX (HPLC-anion exchange) chromatography is performed and the eluents from the product peak are dialysed against excess of Tris-buffer as well as a second dialysis against deionized water. The final products are lyophilized and stored dry.

It is understood that this is one possible method for the synthesis of phosphorothioate-oligodeoxynucleotide. It is clear that improvements and modifications to the description given herein will occur to those skilled in the art and will still fall within the scope of the invention.

Methods for the synthesis of oligo-ribonucleotides are known to those skilled in the art. One possible method using 2'-ACE RNA Chemistry is described by Scaringe, S. A.: "RNA Oligonucleotide Synthesis via 5'-Silyl-2'-Orthoester Chemistry", Methods 23, 206-217, 2001)

It is understood that this is one possible method for the synthesis of oligo-ribonucleotides. It is clear that improvements and modifications to the description given herein will occur to those skilled in the art.

In one embodiment, the antisense oligonucleotides or modifications thereof can be used for the stimulation of the immune system by inhibiting expression and/or functional activity of "Melanoma Inhibitory Activity" MIA.

In another embodiment, the antisense oligonucleotides or modifications thereof are used in a combination with at least one of the molecules, viruses, peptides and/or cell extracts listed under a) to m:
a) molecules selected from the group consisting of chemokines, including lymphotactin and/or immune cell attracting factors;
b) viruses and/or parts of viruses, including adeno-viruses, papilloma viruses, Epstein-Barr-Viruses, viruses that are non-pathogenic including Newcastle-Disease virus, Cowpox-virus;
c) autologous and/or heterologous MHC-molecules;
d) molecules involved in antigen processing;
e) molecules involved in antigen presentation;
f) molecules involved in mediating immune-cell effects;
g) molecules involved in mediating immune cell cytotoxic effects;
h) molecules involved in antigen transportation;
i) co-stimulatory molecules;
j) peptides enhancing recognition by immune cell and/or cytotoxic effects of immune cells;
k) peptides containing one or more amino acids differing between a protein in the target cell from the other cells within an organism including, but not limited to antigens, specific for melanoma cells and/or melanocytes and/or breast cells and/or breast cancer cells; according to the invention the inhibition of the syntheses and/or function of MIA is achieved by using molecule of group I) wherein
l) molecules selected from the group consisting of
  peptides containing one or more mutations and/or amino acid substitutions of the Ras protein amino, the p53 protein, the EGF receptor protein, fusion peptides and/or fusion proteins, the retinoblastoma protein, peptides containing one or more mutations and/or amino acid substitutions and/or amino acid substitutions caused by gene re-arrangements and/or gene translocations, peptides containing one or more mutations and/or amino acid substitutions of proteins coded by oncogenes and/or protooncogenes, proteins coded by anti-oncogenes and/or tumor suppressor genes;
  peptides derived from proteins differing in the target cell by one or amino acids from the proteins expressed by other cells in tile same organism,
  peptides derived from viral antigens and/or coded by viral nucleic acids
  peptides derived from proteins over expressed in the target cell compared to a normal cell
  and combinations thereof m) tumor cell extracts and/or tumor cell lysates and/or adjuvants.

The molecules, including at least one antisense oligonucleotide, viruses, peptides and/or cell extracts listed under a) to m) can be applied by, to the following methods, whereby application is not limited to these methods:
- by vaccination of a human organism with DNA and/or RNA coding for all or part of the molecules listed under a) to m) and/or polypeptides contained in the molecules listed under a) to m)
- by transfection of an human organism and/or transfecting the target cells and/or target pathogens with genes coding for the molecules listed under a) to m)
- parenteral by intravenous, intraarterial, subcutaneous, intraperitoneal or intramuscular injection or infusion and/or locally by oral, epidermal or transdermal administration In a further embodiment, the antisense oligonucleotides or modifications thereof can be combined with an immunostimulatory agent, selected from the group of cytokines and/or inhibitors of the expression and/or function of interleukin-10 and/or transforming growth factor beta (TGF-β) and/or Prostaglandin B2 and/or receptors for Prostaglandin E2 and/or inhibitors of VEGF.

In another embodiment, the antisense oligonucleotides or modifications thereof can be combined with at least one of the following molecules, methods, peptides and/or cell extracts:
- molecules enhancing the immune response against diseased cells or pathogens
- methods and/or molecules enhancing immunogenicity of target cells and/or target pathogens
- immunostimulatory molecules, comprising cytokines including interleukins, such as IL-1, IL-2, IL-4, IL-12, IL-18
- methods for enhancing the expression of cytokines in target cells or pathogens by stimulating their expression and/or by transfecting expression systems into the target cell or target pathogen, capable of expressing these cytokines and/or
- chemokines attracting immune cells including lymphotactin
- methods for enhancing the expression of chemokines in target cells or pathogens by stimulating their expression and/or by transfecting expression systems into the target cell and/or target pathogen, capable of expressing these chemokines
- peptides and/or DNA and/or RNA molecules and or other antigens that are found in tumor cells and/or pathogens, but not in normal cells
- methods for enhancing the expression of peptides and/or antigens that are found in tumor cells and/or pathogens, but not in normal cells
- tumor cell extracts and/or tumor cell lysates and/or adjuvants.

These molecules, including at least one antisense oligonucleotide, peptides and/or cell extracts can be applied parenteral by intravenous, intraarterial, Intraperitoneal, subcutaneous or intramuscular injection or infusion and/or locally by oral, epidermal, intradermal- and transdermal administration. Preferred subjects for application are mammals, most preferred subjects are humans.

In another embodiment, the coding sequences of the antisense oligonucleotides are integrated into a DNA delivery system, comprising viral and/or non-viral vectors together with lipids selected from the group of anionic lipids, cationic lipids, non-cationic lipids and mixtures thereof.

The antisense oligonucleotides thus may contain flanking sequences and/or vector sequences and/or sequences enhancing the expression and/or transfection of the nucleic acid molecules.

In a preferred embodiment of the invention the coding sequences of the antisense oligonucleotides are part of one or more vectors and/or viral sequences and/or viral vectors.

In another embodiment of the invention the antisense oligonucleotides or modifications thereof are coupled to or mixed with folic acid, hormones, steroid hormones such as oestrogene, progesterone, corticosteroids, mineral corticoids, peptides, proteoglycans, glycolipids, phospholipids and derivatives thereof.

In a yet further embodiment, the antisense oligonucleotides or modifications thereof can be used for the preparation of a medicament.

In a more preferred embodiment, the antisense oligonucleotides is combined with one or more of the afore mentioned immunostimulatory agents for the preparation of a medicament, wherein the medicament can be applied locally or systemically to a tumor or other pathologically affected site or organ.

In another embodiment, the medicament is used for the prevention or the treatment of neoplasms and disorders selected from the group of melanoma, gastrointestinal carcinoma, breast cancer, pancreatic cancer, ovarial carcinoma, chondrosarcoma, spinal diseases, cervical myelopathy, lumbar canal stenosis, lumbar disc herniation, rheumatoid arthritis, osteoarthritis, HLA-27-associated oligoarthritis, psoriatic arthritis and rheumatic arthritis, cartilage damage and/or joint destruction.

The effective amount of oligonucleotide applied varies depending upon whether the pharmaceutical composition is used in single or multiple dosages and whether only one or several antisense oligonucleotides are within one pharmaceutical composition.

Dosages given in this writing are for adults. It is quite clear to someone skilled in the art that these dosages have to be adapted if the human being is a child, a person stressed by a further illness or other circumstances.

The effective dosage is dependent also on the method and means of administration.

Routes of administration include, but are not limited to, electrocorporation, epidermal, impression into skin, intra-arterial, intra-articular, intrabuccal, intra-cranial, intra-dermal, intra-lesional, intra-muscular, intranasal, intra-ocular, intra-peritoneal, intra-prostatic, intra-pulmonary, intra-spinal, intrathecal, intratracheal, intra-tumoral, intra-venous, intra-vesical, placement within cavities of the body, nasal inhalation, oral, pulmonary inhalation (e.g., by inhalation or insufflation of powders or aerosols, including by nebulizer), subcutaneous, subdermal, topical (including ophthalmic and to mucous membranes including vaginal and rectal delivery) and transdermal.

In one embodiment subject doses of the oligonucleotides described herein typically range from about 0.05 μg/kg to about 500 mg/kg, preferred about 1 μg/kg to about 100 mg/kg, and more preferred from about 100 μg/kg to about 50 mg/kg per administration, which could be given hourly, daily, weekly, or monthly and any other amount of time therebetween depending on the mode of application.

In some embodiments, however, doses may be used in a range even 2 to 100 fold higher or lower than the typical doses described above. E.g. for oral administration the upper limit of the dosages given above may be up to 1 mg/kg or even up to about 5 mg/kg.

In one embodiment the application of the oligonucleotide in solution is given in continuous infusion, in yet another embodiment several bolus injections or short term infusions of the solution are applied. Doses of the oligonucleotides administered by infusion typically range from about 0.05 μg/kg/day to about 100 mg/kg/day, more preferred from about 1 μg/kg/day to about 50 mg/kg/day, and more preferred from about 100 μg/kg/day to about 30 mg/kg/day. In some embodiments the infusion or bolus injection is repeated about 1 to 100 times or even more, more preferred about 3 to about 30 times and even more preferred 5 to about 10 times.

Short term infusion in the context of this application means infusions from about 0.1 h to about 4 h, more preferred from about 0.5 h to about 3 h and most preferably from about 1 h to about 2 h.

Continuous infusion in the context of this application means infusions from about 5 h up to about 24 h, several days, weeks or even months.

Continuous infusions in special embodiments are repeated about 1 to 100 times and even more, in other embodiments they are repeated about 3 to about 30 times and in yet other embodiments about 5 to about 10 times.

In some embodiments during the time when no oligonucleotide solution is applied, isotonic solutions such as standard infusion solutions, e.g. 0.9% sodium chloride solution, Ringer-lactate solution, dextranes etc. are applied.

Further details of doses used in antisense therapy are reviewed e.g. in Flaherty Current Opinion in Oncology 2001, 13: 499-505, herein incorporated by reference.

The oligonucleotides of this invention are applied purely or in a pharmaceutical acceptable carrier. Pharmaceutical acceptable carrier in the context of this invention means any pharmaceutical composition or formulation suitable for the administration of the oligonucleotide.

In some embodiments compositions and formulations for oral administration include powders or granules, suspensions or solutions in water or non-aqueous media, capsules, sachets or tablets.

In other embodiments compositions and formulations for parenteral application the oligonucleotides are solved in sterile aqueous solutions which may also contain buffers, diluents and other suitable additives e.g. carrier compounds, other pharmaceutically acceptable carriers or excipients.

In yet other embodiments pharmaceutical compositions and formulations for topical administration include transdermal patches, ointments, lotions, drops, creams, gels, sprays, liquids and powders.

In other embodiments pharmaceutical compositions and formulations for rectal administration comprise ointments, creams, gels, suppositories and liquids.

In yet other embodiments pharmaceutical compositions and formulations for nasal administration comprise ointments, creams, gels, drops, sprays liquids and powders.

In embodiments for pulmonary administration pharmaceutical compositions and formulations comprise sprays and powders.

For the above mentioned pharmaceutical compositions and formulations, pharmaceutical carriers, penetration enhancers, aqueous, powder or oily bases, thickeners, flavoring agents, diluents, emulsifiers, dispersing aids, binders and other excipients may be may be added. Compositions and formulations for oral administration in one embodiment are enteric coated.

Besides for therapeutic use the antisense compounds of the invention are useful also for research and diagnostics, because these compounds hybridize to the nucleic acid encoding MIA, enabling sandwich and other assays to easily be constructed to exploit this fact. Hybridization of the antisense oligonucleotides of the invention with a nucleic acid encoding MIA can be detected by means known in the art. Such means may include conjugation of an enzyme to the oligonucleotide, radiolabelling of the oligonucleotide or any other suitable detection means. Kits using such detection means for detecting the level of MIA in a sample may also be prepared.

FIG. 1 discloses the inhibition of MIA expression by different oligonucleotides in HTZ-19 melanoma cells. The bars indicate residual MIA expression of antisense oligonucleotide treated compared to untreated medium control (Medium) or Lipofectin-treated cells (Lipofectin). The numbers 1-8 correspond to the state of art antisense oligonucleotides of the patent application WO 01/68122 having the Sequence ID-No's 1-8 or to the antisense oligonucleotide of the present invention with the sequence 5'-TTG CAT AAA CCC AAG GAG-3' (SEQ ID NO: 1), referred to as "new". The strongest inhibition was achieved with the new antisense oligonucleotide being able to inhibit MIA-expression by 84% compared to the state of art antisense oligonucleotides 1-8 (corresponding to Sequence ID No's 1-8 of the patent application WO 01/68122), where inhibition of MIA-expression varied between 48% and 65%.

FIG. 2a-c discloses the structure of oligonucleotides.

EXAMPLE

Example 1

Inhibition of MIA-secretion by Antisense Oligonucleotides

The efficacy on MIA-inhibition of the antisense oligonucleotide of this invention was compared to those of the state of art which are described in WO 01/68122 with the Sequence-ID-No's 1-8. Therefore, melanoma cells were transfected with oligonucleotides and the MIA-expression in the cell culture supernatant of the cells was measured by enzyme-linked immunosorbent assay.

On day 0, 75.000 cells were seeded in 1 ml medium (DMEM/10% FCS) in a 12-well tissue-culture plate. On days 1 and 2, the cells were transfected with 200 nM of antisense oligonucleotide using Lipofectin (Gibco BRL, Eggenstein, Germany) according to the manufacturers protocol. Each antisense oligonucleotide was transfected in triplicates. At the end of the $2^{nd}$ transfection on day 2, the cells were cultured in DMEM/10% FCS containing 5 μM of the respective antisense oligonucleotide for further three days. The supernatants were taken and stored at −20° C. until quantification of MIA-Protein.

MIA concentrations in the supernatant were measured employing ELISA according to the manufacturers protocol (Roche, Boehringer Mannheim, Germany).

Results:

The strongest inhibition of MIA expression in the supernatant compared to untreated control-cells was achieved with the "new" antisense oligonucleotide SEQ ID NO: 1 of the present invention being able to inhibit MIA-expression by 84% compared to the state of art antisense oligonucleotide described in WO 01/68122 having the SEQ ID NOS: 1-8, where inhibition of MIA-expression varied between 48% and 66%.

What is claimed is:

1. An antisense-oligonucleotide selected from the group consisting of
the sequence 5'-TTG CAT AAA CCC AAG GAG-3' (SEQ ID NO: 1) and modifications excluding base substitutions thereof, and
fragments consisting of subsequences of SEQ ID NO: 1 of at least 8 nucleotides and modifications thereof.

2. The antisense-oligonucleotide according to claim 1 wherein the modification comprises a modified sugar moiety, a modified base, a modified internucleotide linkage, coupling the oligonucleotide to an enhancer of uptake and/or inhibitory activity, and combinations thereof.

3. The antisense-oligonucleotide according to claim 2 wherein the antisense-oligonucleotide is a phosphorothioate oligodeoxynucleotide.

4. The antisense-oligonucleotide according to claim 1 with the structure:

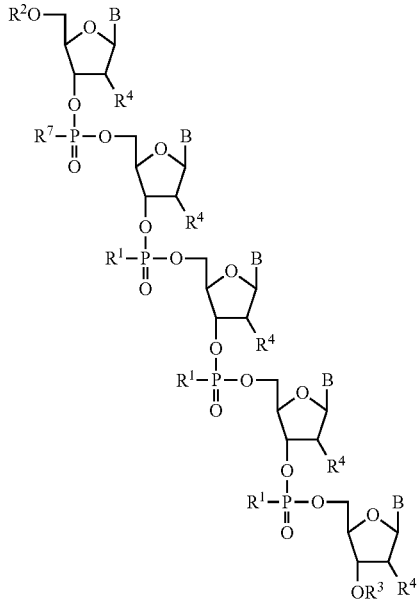

wherein
B=the bases of SEQ ID NO. 1 or the fragments thereof, the bases A, C, G or T in oligodeoxy-ribonucleotides or the bases A, C, G or U in oligo-ribonucleotides;
$R^1$=$OM^+$ ($M^+$=$Na^+$ or $H^+$), $SM^+$=$Na^+$ or $H^+$), $CH_3$, $C_2H_5$, $OCH_3$, or $C_2H_5$; $R^2$ and/or $R^3$ are covalently coupled cholesterol, poly(L)lysine, transferrin or H;
$R^4$=H, F, $CH_3$, $C_2H_5$, OH, $OCH_3$, or $OC_2H_5$;
wherein the structure is a representation of a longer nucleotide chain.

5. The antisense-oligonucleotide according to claim 1 with the formula

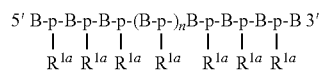

wherein
B=the bases of SEQ ID NO. 1 or the fragments thereof, the bases A, C, G or T in oligodeoxy-ribonucleotides, or the bases A, C, G or U in oligo-ribonucleotides;
p=internucleotide phosphate;
(B—P—)$_n$=an oligodeoxy-ribonucleotide or oligo-ribonucleotide stretch wherein n=1-11;
and wherein R1, encompassing $R^{1a}$ or $R^{1b}$, is varied at the internucleotide phosphates within one oligonucleotide wherein $R^{1a}$=$S^-M^+$, wherein all $M^+$ is $Na^+$ or $H^+$ and $R^{1b}$=$O^-M^+$, wherein all $M^+$ is $Na^+$ or $H^+$; or
$R^{1a}$=$CH_3$ and $R^{1b}$=$O^-M^+$, wherein all $M^+$ is $Na^+$ or $H^+$; or $R^{1a}$=$S^-M^+$, wherein all $M^+$ is $Na^+$ or $H^+$ and $R^{1b}$=$CH_3$; or $R^{1a}$=$CH_3$ and $R^{1b}$=$S^-M^+$, wherein all $M^+$ is $Na^+$ or $H^+$.

6. The antisense-oligonucleotide according to claim 1 with the formula
wherein
B=one of the bases of SEQ ID NO. 1 or the fragments thereof, the bases A, C, G or T in oligodeoxy-ribonucleotides or the bases A, C, G or U in oligo-ribonucleotides;
p=internucleotide phosphate;
(B-p-B-p)$_n$=an oligodeoxy-ribonucleotide or oligo-ribonucleotide stretch wherein
n=2-7; and wherein R1 is alternated at the internucleotide phosphates within one oligonucleotide wherein $R^1a$=$S^-M^+$, wherein all $M^+$ is $Na^+$ or $H^+$ and $R^{1b}$=$O^-M^+$, wherein all $M^+$ is $Na^+$ or $H^+$; or
$R^{1a}$=$CH_3$ and $R^{1b}$=$O^-M^+$, wherein all $M^+$ is $Na^+$ or $H^+$; or $R^{1a}$=$S^-M^+$, wherein all $M^+$ is $Na^+$ or $H^+$ and $R^{1b}$=$CH_3$.

7. A method comprising providing the antisense-oligonucleotide of claim 1, whereby the antisense oligonucleotide results in at least one of the inhibition of expression and/or functional activity of melanoma inhibitory activity (MIA), reducing invasion and/or metastasis, or stimulating immune cells and/or the immune system.

8. A pharmaceutical composition comprising an antisense-oligonucleotide according to claim 1.

9. The pharmaceutical composition according to claim 8 wherein the antisense-oligonucleotide is integrated into a DNA delivery system comprising viral and/or non-viral vectors together with lipid acids or derivatives thereof selected from the group consisting of anionic lipids, cationic lipids, non-cationic lipids, and mixtures thereof.

10. The pharmaceutical composition according to claim 8 further comprising an immunostimulatory agent.

11. The pharmaceutical composition according to claim 10 wherein the immunostimulatory agent is selected from the group consisting of cytokines, inhibitors of expression and/or function of interleukin-10, inhibitors of expression and/or function of transforming growth factor beta (TGF-β), inhibitors of expression and/or function of Prostaglandin B2, inhibitors of expression and/or function of receptors for Prostaglandin E2, inhibitors of VEGF, and combinations thereof.

12. A method comprising providing the pharmaceutical composition according to claim 8 in a method for the treatment of at least one of neoplasms, infections, or immunosuppressive disorders.

13. A method comprising providing the pharmaceutical composition according to claim 8 for the treatment of at least one disorder, neoplasm, infection, or immunosuppressive disorder wherein abnormal expression of melanoma inhibitory activity plays a role in the disorder, neoplasm; infection, or immunosuppressive disorder.

14. A method comprising providing the pharmaceutical composition according to claim 8 for the treatment of neoplasms and/or disorders selected from the group consisting of melanoma, gastrointestinal carcinoma, breast cancer, pancreatic cancer, ovarian carcinoma, chondrosarcoma, spinal diseases, cervical myelopathy, lumbar canal stenosis, lumbar disc herniation, rheumatoid arthritis, osteoarthritis, HLA-27-associated oligoarthritis, psoriatic arthritis, rheumatic arthritis, cartilage damage, joint destruction, and combinations thereof.

15. A diagnostic composition comprising an antisense-oligonucleotide according to either claim 1 or claim 2.

16. The antisense oligonucleotide of claim 5 wherein $(B-p-)_n=$an oligodeoxy-ribonucleotide or oligo-ribonucleotide stretch wherein n=1-11.

17. The antisense oligonucleotide of claim 6 wherein $(B-p-B-p)_n=$an oligodeoxy-ribonucleotide or oligo-ribonucleotide stretch wherein n=3-7.

\* \* \* \* \*

UNITED STATES PATENT AND TRADEMARK OFFICE
CERTIFICATE OF CORRECTION

| | | |
|---|---|---|
| PATENT NO. | : 7,910,563 B2 | Page 1 of 1 |
| APPLICATION NO. | : 10/567879 | |
| DATED | : March 22, 2011 | |
| INVENTOR(S) | : Schlingensiepen et al. | |

It is certified that error appears in the above-identified patent and that said Letters Patent is hereby corrected as shown below:

On the Title page

Item (86) "PCT/EP2004/006986" should read, -- PCT/EP2004/008986 --

Column 14 Claim 5

Lines 25 -29, $$5'\quad B\text{-}p\text{-}B\text{-}p\text{-}B\text{-}p\text{-}(B\text{-}p\text{-})_n B\text{-}p\text{-}B\text{-}p\text{-}B\text{-}p\text{-}B \quad 3'$$
$$\quad\quad |\quad |\quad |\quad |\quad\quad |\quad |\quad |$$
$$\quad R^{1a}\ R^{1a}\ R^{1a}\ R^{1a}\quad R^{1a}\ R^{1a}\ R^{1a}$$

should read:

$$5'\quad B\text{-}p\text{-}B\text{-}p\text{-}B\text{-}p\text{-}(B\text{-}p\text{-})_k B\text{-}p\text{-}B\text{-}p\text{-}B\text{-}p\text{-}B \quad 3'$$
$$\quad\quad |\quad |\quad |\quad |\quad\quad |\quad |\quad |$$
$$\quad R^{1a}\ R^{1a}\ R^{1a}\ R^{1b}\quad R^{1a}\ R^{1a}\ R^{1a}$$

-- --

Line 45, insert the following before "wherein"

$$5'\quad B\text{-}p\text{-}B\text{-}p\text{-}(B\text{-}p\text{-}B\text{-}p\text{-})_m B\text{-}p\text{-}B \quad 3'$$
$$\quad\quad |\quad |\quad\quad |\quad |\quad\quad |$$
$$\quad R^{1a}\ R^{1a}\ R^{1b}\ R^{1a}\ R^{1b}$$

-- --

Column 16

Claim 16, Line 15, "The antisense oligonucleotide" should read
-- The antisense-oligonucleotide --

Claim 17, Line 18, "The antisense oligonucleotide" should read
-- The antisense-oligonucleotide --

Signed and Sealed this
Thirteenth Day of September, 2011

David J. Kappos
*Director of the United States Patent and Trademark Office*

SEQUENCE LISTING

<160> NUMBER OF SEQ ID NOS: 1

<210> SEQ ID NO 1
<211> LENGTH: 18
<212> TYPE: DNA
<213> ORGANISM: Artificial
<220> FEATURE:
<223> OTHER INFORMATION: antisense oligonucleotide of the human Melanoma Inhibitory Activity polypeptide

<400> SEQUENCE: 1
ttgcataaac ccaaggag         18